(12) United States Patent
Chao

(10) Patent No.: US 6,245,528 B1
(45) Date of Patent: Jun. 12, 2001

(54) LATENT BACULOVIRUS EXPRESSION SYSTEM

(75) Inventor: Yu-Chan Chao, Taipei (TW)

(73) Assignee: Academia Sinica (TW)

( * ) Notice: Subject to any disclaimer, the term of this patent is extended or adjusted under 35 U.S.C. 154(b) by 0 days.

(21) Appl. No.: 09/361,474

(22) Filed: Jul. 27, 1999

Related U.S. Application Data

(60) Provisional application No. 60/094,411, filed on Jul. 28, 1998.
(51) Int. Cl.[7] .................. C12N 15/866; C12N 15/63; C12N 15/64; C12N 15/34
(52) U.S. Cl. .................. 435/69.1; 435/320.1; 435/235.1; 435/455; 435/456; 435/91.1; 435/91.42; 435/91.32
(58) Field of Search .................. 435/320.1, 235.1, 435/69.1, 69.8, 455, 456, 91.1, 91.42, 91.32

(56) References Cited

PUBLICATIONS

Lerch et al., Nucleic Acids Res., vol. 21, No. 8, pp. 1753–1760, 1993.*

Chao, Yu–Chan et al., "A 2.9–Kilobase Noncoding Nuclear RNA Functions in the Establishment of Persistent Hz–1 Viral Infection," Journal of Virology, vol. 72, No. 3, p. 2233–2245, 1998.

Chao, Yu–Chan et al., "Differential Expression of Hz–1 Baculovirus Genes during Productive and Persistent Viral Infections," Journal of Virology, vol. 66, No. 3, p. 1442–1448, 1992.

Clem, Rollie J. et al, "Prevention of Apoptosis by a Baculovirus Gene During Infection of Insect Cells," Science, vol. 254, p. 1388–1390.

Clem, Rollie J. et al., "Influence of Infection Route on the Infectivity of Baculovirus Mutants Lacking the Apoptosis–Inhibiting Gene . . . ," Journal of Virology, vol. 68, No. 10, p. 6759–6762, 1994.

Crook, Norman E. et al., "An Apoptosis–Inhibiting Baculovirus Gene with a Zinc Finger–Like Motif," Journal of Virology, vol. 67, No. 4, p. 2168–2174, 1993.

Hershberger, Pamela A. et al., "Site–Specific Mutagenesis of the 35–Kilodation Protein Gene Encoded by *Autographa californica*, Nuclear . . . ," Journal of Virology, vol. 66, No. 9, p. 5525–5533, 1992.

Lee, Jin–Ching et al., "Superinfection–Induced Apoptosis and Its Correlation with the Reduction of Viral Progeny in Cells Persistently . . . ," Journal of Virology, vol. 67, No. 12, p. 6989–6994, 1993.

Prikhod'ko, Elena A. et al., "Induction of Apoptosis by Baculovirus Transactivator IE1," Journal of Virology, vol. 70, No. 10, p. 7116–7124, 1996.

* cited by examiner

*Primary Examiner*—David Guzo
(74) *Attorney, Agent, or Firm*—Fish & Richardson P.C.

(57) ABSTRACT

The invention relates to a baculovirus including a disruption in its endogenous p35 gene and its use in establishing latent baculovirus infections. In some embodiments, the baculovirus can also include a sequence encoding a non-baculovirus RNA and a baculovirus early gene promoter which drives expression of the non-baculovirus RNA.

24 Claims, 1 Drawing Sheet

LATENT BACULOVIRUS EXPRESSION SYSTEM

CROSS REFERENCE TO RELATED APPLICATIONS

This application claims priority from U.S. Provisional Application Serial No. 60/094,411, filed Jul. 28, 1998.

BACKGROUND OF THE INVENTION

Viruses of the family Baculoviridae, commonly known as baculoviruses, are lethal pathogens of insects of the order Lepidoptera. These viruses typically kill their hosts by productive, lytic infection in insect tissues.

Baculoviruses generally contain a covalently closed, circular double-stranded DNA genome of about 90 to 160 kb in length. This genome is capable of accommodating relatively long heterologous sequences. In addition, a high level of structural viral protein synthesis is achieved during productive infection. Consequently, the baculovirus/insect cell system has become a popular protein expression vehicle for academic research and industrial applications. However, since high level expression is coincident with productive infection and late gene expression, the baculovirus expression system is limited by the eventual death of the baculovirus-infected culture.

SUMMARY OF THE INVENTION

The invention is based on the discovery that a baculovirus containing a disruption in its endogenous p35 gene is able to establish a persistent infection (i.e., an infection in which the host are not lysed. Consequently, a persistent baculovirus expression culture system can be established by infecting any suitable host cell with a baculovirus having a disrupted p35 gene and an exogenous gene driven by a baculovirus early promoter (i.e., any promoter able to drive baculovirus expression in latent infection).

It was also discovered that cells harboring the p35-disrupted viruses are resistant to baculovirus super infection, i.e., infection by a second baculovirus. Thus, the p35-disrupted baculoviruses can be used to protect insects, especially commercially valuable insects (e.g., silkworms) from pathogenic baculoviruses.

Accordingly, the invention features a baculovirus including a disruption in its endogenous p35 gene. The baculovirus can further include a first sequence encoding a first RNA (e.g., a non-baculovirus RNA) and a baculovirus early gene promoter (e.g., an immediate early gene promoter) which drives expression of the first RNA. The first RNA can be a mRNA encoding a first protein (e.g., a non-baculovirus protein), such as a detectable protein (e.g., βgalactosidase). The baculovirus can optionally also include a second sequence encoding a second non-baculovirus RNA. The second non-baculovirus RNA can be a mRNA encoding a second protein (e.g., a non-baculovirus protein), such as a selectable protein. A detectable protein is a protein whose expression is readily detectable, e.g., by fluorescent, luminescent, or chromogenic assays. A selectable protein is a protein whose expression confers a selectable phenotype on a cell. An example of a selectable phenotype is resistance to an antibiotic or antimitotic drug, such as neomycin or G418. Under some circumstances it can be useful to drive expression of the second protein from a baculovirus constitutive promoter, such as when the second protein confers drug resistance.

A baculovirus early promoter (e.g., a promoter derived from the baculovirus pagi gene) is a promoter, in the context of a baculovirus genome, that can drive expression in the early stage of the virus life cycle, i.e., just after viral entry and before expression of most viral structural proteins. A baculovirus constitutive promoter (e.g., a promoter derived from a heat shock protein-70 [hsp70] gene) is a promoter, in the context of a baculovirus genome, that can drive expression in all stages of the virus life cycle. A baculovirus early promoter or a baculovirus constitutive promoter is not necessarily derived from a baculovirus genome. Promoters derived from the genome of other organisms and viruses are useful in the baculovirus of the invention, as long as they satisfy the above constraints.

The invention also includes methods of expressing a non-baculovirus RNA or a non-baculovirus protein by introducing a baculovirus of the invention into a cell.

The invention also features a method of inhibiting baculovirus super infection in a cell by introducing into the cell a first baculovirus including a disruption in its endogenous p35 gene, and exposing the cell to a second baculovirus. By "exposing a cell to a second baculovirus" is meant placing the cell, or an organism containing the cell (e.g., a silkworm), in an environment suspected or known to contain a baculovirus. The environment can be artificial (e.g., a culture dish to which a baculovirus has been added) or in the wild (e.g., a forest where pathogenic baculoviruses are known to exist). As used herein, the term "inhibiting" includes both complete inhibition and partial inhibition.

A disruption of a gene is any deletion (e.g., deletion of a promoter sequence), insertion, or other mutation in the gene which renders the gene non-functional due to loss or misdirection of transcription, loss or misdirection of translation, or loss of an amino acid sequence necessary for protein function.

The baculoviruses and methods of the invention provide a new eukaryotic protein expression system useful in both academic and industrial settings. Unlike previous baculovirus expression systems, which are characterized by a self-limiting lytic infection, the expression systems made possible by the baculoviruses and methods of the invention utilize persistent, baculovirus-infected cultures. In addition, the baculoviruses described herein can be used to establish cells resistant to baculovirus super infection, a first step in protecting commercially valuable insects from baculovirus-induced disease.

Other features or advantages of the present invention will be apparent from the following drawings and detailed description, and also from the claims.

DETAILED DESCRIPTION

Figure 1:
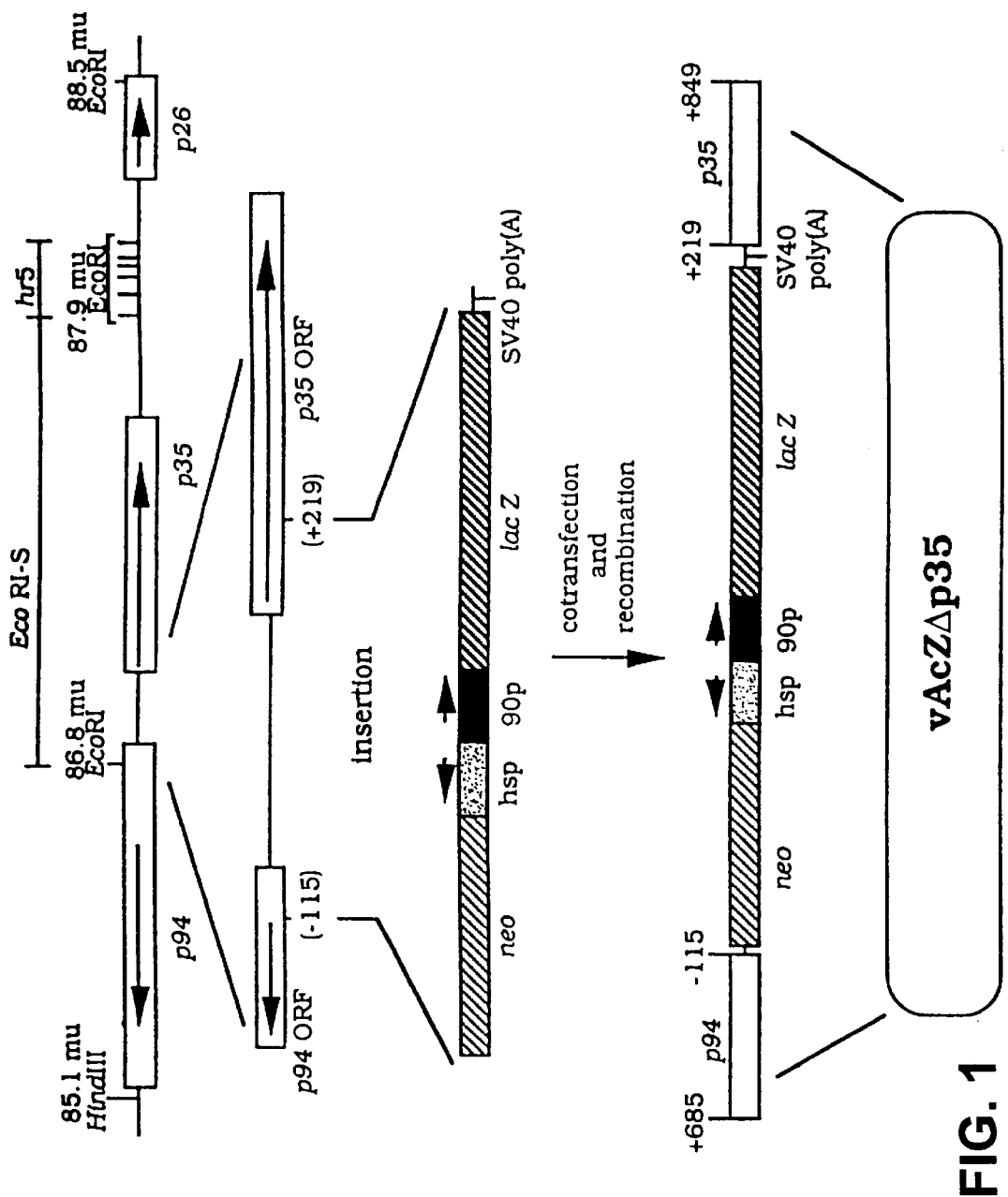
FIG. 1 is a schematic representation of a region of a baculovirus genome in which the p35 gene has been disrupted and a lacZ and neo gene introduced.

The invention relates to baculoviruses having a disrupted p35 gene. These baculoviruses establish latent viral infections in insect cells, leading to two important results. First, baculovirus persistency can be used to express proteins in persistent cultures. Second, baculovirus persistency blocks infection by subsequent baculoviruses. This latter observation provides a means for protecting commercially valuable insects from baculovirus-induced disease.

Standard procedures for cloning baculoviruses having a disrupted p35 gene and introducing them into cells to establish a persistent infection are well known in the art.

persistent infections in lepidopterans can be achieved by feeding insect larvae a diet contaminated with baculovirus having a disrupted p35 gene (see, e.g., Clem et al., J Virol 68:6759–6762, 1994).

Without further elaboration, it is believed that one skilled in the art can, based on the above disclosure and the description below, utilize the present invention to its fullest extent. The following example is to be construed as merely illustrative of how one skilled in the art can practice the invention and are not limitative of the remainder of the disclosure in any way. Any publications cited in this disclosure are hereby incorporated by reference.

I. Disruption of the p35 Gene in Baculovirus Allow Persistence of Infected Cells Two Autographa californica multiple nuclear polyhedrosis viruses (AcMNPVs) carrying mutations at the p35 gene locus were used in the following example. vAcZΔp35 was constructed as shown schematically in FIG. 1. The lacZ and neo genes were inserted into plasmid pTSV (Lee et al., Nucl Acids Res 22:4683–4689, 1995) to create plasmid pThsN90Z. The neo gene was driven by the Drosophila hsp70 promoter (Steller et al., Mol Cell Biol 6:1640–1649, 1986), while the lacZ gene was driven by the pag-90 promoter, an immediate early type-promoter derived from pag1 of the Hz-1 virus (Chao et al., J Virol 72:2233–2245, 1998). Both genes were flanked by p94 and p35 gene sequences by inserting homologous regions of the baculovirus p94 gene (801 bp, nucleotides −115 to +685 relative to the p94 ATG start codon) and p35 (631 bp, nucleotides +219 to +849 relative to the p35 ATG start codon) into plasmid pThsN90Z to produced transfer vector pTΔ35hsN90Z. These p94- and p35-specific fragments were generated by PCR, and their sequences were confirmed by DNA sequencing.

Homologous recombination was carried out by co-transfecting both AcMNPV genomic DNA and plasmid pTΔ35hsN90Z into TN368 cells. The recombinant virus, named vAcZΔp35, was cloned by screening the transfected TN368 cells for blue plaques with occlusion bodies following X-gal staining and was further verified in infected Sf21 cells by the lack of occlusion body formation. Antibiotic G418 (2 mg/ml) was used in all screenings to eliminate any wild-type virus. The recombinant viruses were further verified by restriction mapping of their genomic DNA and by their induction of apoptosis upon infection in Sf21 cells.

The second AcMNPV used in this example is vAcAnh, called the annihilator, as described in Clem et al., Science 254:1388–1390, 1991. This virus contains a 754 bp deletion in the p35 gene, resulting in a truncated p35 protein which is missing 132 amino acids from its carboxyl terminus.

For complementation studies, the p35 expression plasmid pKi$^h$35 hN was created. This plasmid contains a complete open reading frame of the p35 gene driven by the ie1 gene promoter of AcMNPV. A hr5 enhancer sequence of 677 bp in length (Guarino et al., J Virol 60:215–223, 1986) was inserted upstream of the ie1 promoter. The neo gene is driven by the Drosophila hsp70 promoter described above. To produce p35-expressing cell lines, pKi$^h$35 hN was transfected into insect cells using CellFECTIN™ (Life Technologies). Neomycin-resistant clones were cultured in the presence of 2 mg/ml G418 for two weeks, and three individual clones were isolated.

For infection experiments, S. frugiperda (fall armyworm) cell lines Sf9 and Sf21AE, and Trichoplusia ni (cabbage looper) cell line TN368 were maintained at 26° C. in TNM-FH medium supplemented with 8% fetal bovine serum (Life Technologies). Viruses were each propagated in TN368 cells. Titers of the viruses were estimated by plaque assays using TN368 cells.

When Sf21 cells were infected by the vAcAnh virus or the vAcZΔp35 virus, most of the cells were lysed via apoptosis. The surviving cells gave rise to persistently infected cell clones seven days post-infection. Infection by the wild type virus or by a Cp-iap rescued-p35 mutant vAsB6-1 (Birnbaum et al., J Virol 68:2521–2528, 1994) did not result in persistent clones. Thus, the repression of persistent viral infection is not due to a specific p35 function, but instead is more likely due to a general effect related directly or indirectly to the blocking of cellular apoptosis.

In order to confirm that p35 blocks persistent viral infection, $4 \times 10^4$ Sf21 cells stably transfected with pKi$^h$35 hN were infected with vAcAnh at a multiplicity of infection (moi) of 50. At seven days post-infection, viral occlusion bodies were clearly visible, suggesting that functional p35 was produced in these cells in an amount sufficient to complement the defect in vAcAnh. These cultures never yielded persistent clones, indicating that persistent viral infection was dependent on a lack of function for p35 rather than any cis effect of the p35 gene locus in the viral genome.

The capacity of various p35 mutants to establish persistently infected cell clones was evaluated. Parental cells (Sf9 or Sf21) were seeded at a density of $4 \times 10^4$ cells per well in a 96-well plate and infected with Hz-1, AcMNPV, vAcAnh, vAcZΔp35, or vAsB6-1 at various moi. Seven to ten days after infection, the number of surviving cells was determined by trypan blue exclusion. Cell clones containing more than five cells were registered as a viable clone. These cells were propagated to form monolayers where possible. Although some of the clones died during propagation, the number of the original colonies formed by the infection of a certain virus at a certain concentration remained a valid measure of the colony formation potential of the individual viruses.

Only vAcAnh and vAcZΔp35 could generate persistently infected clones. These clones were not observed in cells infected with wild type or vAsB6-1 viruses in a wide range of titers. In these experiments, higher moi generated more colonies suggesting that specific virus gene product(s) enhance the formation of persistently infected clones. Again, this result was consistent with the conclusion that p35 blocks entry into viral persistency.

II. Persistently Infected Clones Retain Viral DNA

To establish in culture specific clones persistently infected with baculovirus, $2 \times 10^5$ cells per well in a 24-well plate were inoculated with vAcAnh or vAcZΔp35 at a moi of 50. Two weeks post-inoculation, the surviving cell clones became visible. Clones were isolated, transferred into a 96-well plate, and grown for 7–10 days with the medium changed once every 3–4 days.

The surviving clones were each transferred to a 24-well plate and, if still growing, to larger plates or flasks. On average, about 3–6 clones per 10 original clones survived these transfers. Clones were apparently lost in passage due to apoptosis. These clones were grown in a medium consisting of 50% fresh medium and 50% conditioned medium.

Two groups of persistently infected cell lines were established and used in subsequent experiments. Four persistently infected cell lines derived from infection with vAcAnh were named Sf9-vAc-1, Sf9-vAc-2, Sf9-vAc-3, and Sf21-vAc-1. Three persistently infected cell lines derived from infection with vAcZΔp35 were named Sf9-vAcZΔp35-1, Sf9-vAcZΔp35-2, and Sf9-vAcZΔp35-3.

To detect very low amounts of viral DNA in persistently infected cells, DNA was amplified directly from cultured cells by PCR. Cells were washed twice in phosphate buffered saline (PBS) and diluted to $10^6$ cells/ml. Ten microliters of this diluted suspension were lysed by adding 90 μl of detergent buffer (50 mM KCl, 10 mM Tris-HCl (pH 8.3), 0.1 mg/ml gelatin, 0.45% NP-40, 0.45% Tween-20, 0.6 mg/ml proteinase K). The diluted suspension was then incubated at 60° C. for one hour. After the incubation, the proteinase K was inactivated at 95° C. for 15 minutes.

Ten microliters of this lysate were amplified by PCR and analyzed by agarose gel electrophoresis. Serial 10-fold dilutions of plasmid pThsN90Z were used as molecular standards. The plasmid DNA was amplified simultaneously with the cell lysates to determine the quantity of viral DNA in the cells persistently infected with vAcAnh. Two negative controls, including a reaction mixture without template DNA and a reaction containing only Sf9 cell lysate, were used to ensure no contaminating template in the reagents.

The primers were complementary to the 5' and 3' regions of the 801-bp fragment of the p94 gene. PCR products were fractionated on a 1.5% agarose gel and transferred by vacuum blotter (Vacu GeneXL; Pharmacia LKB Biotechnology) onto a nylon membrane. The membranes were probed with a p94 gene fragment labeled with [$\alpha-^{32}P$] dCTP by random priming (Berhringer-Mannheim).

To determine the presence of viral DNA in cell cultures, total genomic DNAs were purified from uninfected and persistently infected cells and blotted onto nylon membranes using the Hybri-Dot Manifold (Bio-Rad Laboratories). The membranes were probed with viral DNA labeled with [$\alpha-^{32}p$] dCTP by random priming. The blot was visualized by auto radiography and further quantified using a PhosphorImager (Molecular Dynamics).

Finally, viral transcripts were detected as follows. Total cellular RNA was prepared from different cell clones using Ultraspec RNA isolation reagent (Biotecx). To detect the expression of various immediate early genes, 10 μg of total RNA was reverse transcribed using an oligo d(T) primer and moloney murine leukemia virus (MMLV)-reverse transcriptase. Equal amounts of cDNA were amplified by PCR with specific primers for viral ie0, ie1, and ie2 genes, and cellular gaped genes.

The primers used for PCR were as follows: ie0, GGCAACGCAACATGATAAGAC (SEQ ID NO:1) and GTTCAAGGGTTGCACAGCTT (SEQ ID NO:2), which are complementary to sequences –11 to +720 relative to the ATG start codon of ie0; and ie1, ATCGTGAACAAC-CAAGTGA (SEQ ID NO:3) and GTTCAAGGGTTGCA-CAGCTT (SEQ ID NO:4), which are complementary to sequences –22 to +520 relative to the ATG start codon of ie1 (Chisolm et al., J Virol 62:3193–3200, 1988); ie2, AACAG-TATCCTACCAGCCCA (SEQ ID NO:5) and CCTCTACT-TCTTCTTCGGGT (SEQ ID NO:6), which are complementary to sequences –23 to +612 relative to the ATG start codon of ie2 (Carson et al., Virology 182:279–286, 1991); and GAPDH, GACGGACCCTCTGGAAAA (SEQ ID NO:7) and ACCAGCTGATGAGCTTGAC (SEQ ID NO:8), which correspond to amino acid residues 195 to 310 of the Drosophila melanogaster gaped gene (Lu et al., J. Virol 69:975–982, 1995).

Each PCR was carried out for 30 cycles. Samples without MMLV-reverse transcriptase were also tested to ensure that the fragment was amplified from mRNA. The RT-PCR products were separated by electrophoreses on 1.2% agarose gels and transferred to a MAGNA nylon transfer membrane (MSI) using a vacuum blotter (Vacu GeneXL; Pharmacia LKB Biotechnology). The membrane was hybridized separately with $^{32}P$-labeled probes against ie0, ie1, ie2, and gapdh genes at 60° C. overnight in hybridization buffer containing 0.25 M $Na_2HPO_4$ (pH 7.2), 1 mM EDTA, 7% SDS, 1% BSA fraction V, and 10% formamide.

In all the persistently infected cells infected by vAcAnh, viral DNA was detectable by PCR, followed by Southern hybridization after 80 passages. After prolonged serial passages, still higher levels of viral DNA content were detected by Southern analysis in Sf9-vAcZΔp35-1, Sf9-vAcZΔp35-2, the vAcAnh-infected cells. Dot blot hybridizations confirmed this general trend.

In addition, the expression of viral early genes was monitored using RT-PCR. The expression of these early genes was detectable in Sf9 cells initially infected by the wild type AcMNPV. Early gene expression was also apparent in cells newly infected with the annihilator vAcAnh before latency was established. No early gene expression was detected in cells persistently infected by vAcAnh. In contrast, most of the viral early genes were expressed in persistent cell lines Sf9-vAcZΔp35-1 and Sf9-vAcZΔp35-2 established by vAcZΔp35. The expression of all the tested early genes from these two cell lines were relatively strong and not distinguishable from the early gene expression of cells productively infected by wild type viruses, suggesting that the viral genome was maintained in an inactive state within the infected cells. It was also believed that expression of exogenous p35 could release the block to productive infection; this supposition was tested as described below. The expression of early genes was not detected in Sf9-vAcZΔp35-3 cells.

III. Non-Baculovirus Protein is Expressed In Baculovirus Latency

To determine whether β-galactosidase was expressed in cells infected with vAcZΔp35, cells were fixed for five minutes at room temperature in a solution containing 2% formaldehyde, 2% glutaraldehyde, 150 mM NaCl, and 15 mM $Na_2HPO_4$. Cells were then washed twice with a solution of 150 mM NaCl and 15 mM $Na_2HPO_4$, and stained with a solution containing 1 mg/ml 5-bromo-4-chloro-3-indolyl-β-D-galactopyranoside, 5 mM $K_3Fe(CN)_6$/$K_4Fe(CN)_6$, and 5 mM $MgCl_2$. The cells were stained overnight at 37° C. before microscopic examination for blue cells, which are indicative for lacZ expression.

Essentially all infected cells exhibited initial lacZ activity after infection with vAcZΔp35. During early passages, some 10%–20% of the cells died via apoptosis. At passage 5, the percentage of total cells in culture that were apoptotic began to decrease, while about 50% of the cells expressed lacZ. These persistently infected cells grew slower than did the parental cells, with a doubling time of roughly 27–30 hours. The lacZ activity was observed for 50–60 passages over a period of five to six months.

IV. Persistent Baculovirus Infection Protects Cells from Superinfection

Parental and persistently infected cells were challenged with either vAcAnh or wild type AcMNPV at passage 90. Both the parental cells and persistently infected cells were challenged with AcMNPV or vAcAnh at an moi of 10, 1, and 0.1. After adsorption, the residual viruses were removed, and the cells were incubated with culture medium at 26° C.

for three days. Viability of the cells was estimated by trypan-blue exclusion.

Sf9 and Sf21 cells were fully susceptible to challenge, even at an moi of 0.1, as indicated by the near total death of the culture three days after challenge. Partial resistance to the infection of these two viruses was observed in Sf9-vAc-1 and Sf9-vAc-2. A challenge at a moi of 10 resulted in close to 100% death, the challenges at an moi of 0.1 led to only about 10% dead cells after three days. Resistance to challenge was far less evident in Sf9-vAc-3 and Sf21-vAc-1, though a significant reduction in the percentage of dead cells, relative to Sf9 and Sf21, could be seen at a moi of 0.1.

Significant viral resistance was observed in cells persistently infected with vAcZΔp35. In general, less than 5% of the cells were dead three days post-challenge at any of the above moi. Clearly, baculoviruses with disrupted p35 genes could inhibit super infection by lytic baculoviruses.

V. p35 Can Reactivate Virus Production in Persistently Infected Cells

No infectious virus could be detected in Sf2l-vAc-1, Sf9-vAc-1, Sf9-vAc-2, or Sf9-vAc-3. Low viral titers could be detected in the cultures of two persistent cell lines, Sf9-vAcZΔp35-1 and Sf9-vAcZΔp35-2, but not in Sf9-vAcZΔp35-3 cells.

To further study whether infectious virus could be reactivated from these persistently infected cells, we transfected p35 expression vector pKi$^h$35 hN into the persistently infected cell lines. Persistently infected cells ($2\times10^5$ cells/well in 24-well plates) were transfected with 1 μg of plasmid pKi$^h$3 hN as described above. As a control, parental Sf9 cells were transfected with pKi$^h$35 hN. At 24 hours post-transfection, these cells were infected with vAcZΔp35 at a moi of 10. The culture media were harvested at six days post-transfection, and the titers of released viruses were determined by a plaque assay using TN368 cells.

The positive control culture resulted in abundant production of infectious virus. Yields of viral progeny from Sf9-vAcZΔp35-1 and Sf9-vAcZΔp35-2 cells transfected with the p35 expression plasmid were increased, although not dramatically on a log scale. On the other hand, the yield of virus from Sf9-vAcZΔp35-3 cells transfected with the p35 expression plasmid was dramatically increased by several logs. Another non-virus-producing persistent cell line, Sf9-vAcZΔp35-4 (established at a date later than that for the first three clones) yielded abundant virus after transfection of the p35 expression plasmid.

These observations indicate that the persistent baculovirus-infected cells were genuinely latent, since production of viruses could be triggered by expressing p35, thereby releasing the block from latency to productive infection.

Other Embodiments

It is to be understood that while the invention has been described in conjunction with the detailed description thereof, the foregoing description is intended to illustrate and not limit the scope of the invention, which is defined by the scope of the appended claims. Other aspects, advantages, and modifications are within the scope of this invention.

For example, although the disruption of the p35 gene and the introduction of one or more non-baculovirus genes are achieved by one single replacement of a baculovirus genomic sequence, other genomic modifications are within the scope of the claims. The introduction of a sequence encoding a non-baculovirus RNA or protein can be at any position within a genome that already has a disrupted p35 gene.

What is claimed is:

1. A recombinant baculovirus comprising a disruption in its endogenous p35 gene, a sequence encoding a non-baculovirus RNA, and a baculovirus constitutive promoter that drives expression of the RNA.

2. The baculovirus of claim 1, wherein the disruption is a deletion of a portion of the p35 gene.

3. The baculovirus of claim 1, wherein the non-baculovirus RNA is a mRNA encoding a protein.

4. The baculovirus of claim 1, wherein the baculovirus constitutive promoter is a hsp70 promoter.

5. A method of expressing a RNA in a cell, the method comprising introducing the baculovirus of claim 1 into the cell, culturing the cell, and expressing the RNA in the cell.

6. The baculovirus of claim 2, wherein the portion of the p35 gene comprises the p35 promoter.

7. The baculovirus of claim 3, wherein the protein is a non-baculovirus protein.

8. A method of inhibiting baculovirus superinfection in a cell, the method comprising introducing into the cell a first baculovirus comprising a disruption in its endogenous p35 gene, and exposing the cell to a second baculovirus.

9. The method of claim 8, wherein the disruption is a deletion of a portion of the p35 gene.

10. The method of claim 9, wherein the portion of the p35 gene comprises the p35 promoter.

11. A method of establishing a persistent baculovirus infection in a cell, the method comprising introducing into the cell a baculovirus comprising a disruption in its endogenous p35 gene, and culturing the cell to establish the persistent baculovirus infection.

12. A method for producing a RNA, the method comprising introducing into a cell a baculovirus comprising (1) a disruption in its endogenous p35 gene, (2) a sequence encoding the RNA, and (3) a promoter which drives expression of the RNA; culturing the cell to establishing a culture persistently infected with the baculovirus; and expressing the RNA in the culture.

13. The method of claim 12, wherein the disruption is a deletion of a portion of the p35 gene.

14. The method of claim 13, wherein the portion comprises the p35 gene promoter.

15. The method of claim 12, wherein the promoter is a baculovirus early gene promoter.

16. The method of claim 12, wherein the promoter is a baculovirus constitutive promoter.

17. The method of claim 12, wherein the polypeptide is a non-baculovirus polypeptide.

18. A recombinant baculovirus comprising a disruption in its endogenous p35 gene, a sequence encoding an RNA, and a non-baculovirus promoter that drives expression of the RNA in all stages of the baculovirus life cycle.

19. The baculovirus of claim 18, wherein the RNA is a non-baculovirus RNA.

20. The baculovirus of claim 19, wherein the non-baculovirus RNA is a mRNA encoding a protein.

21. The baculovirus of claim 20, wherein the protein is a non-baculovirus protein.

22. The baculovirus of claim 18, wherein the disruption is a deletion of a portion of the p35 gene.

23. The baculovirus of claim 18, wherein non-baculovirus promoter is a hsp70 promoter.

24. A method of expressing a RNA in a cell, the method comprising introducing the baculovirus of claim 18 into the cell, culturing the cell, and expressing the RNA in the cell.

* * * * *

SEQUENCE LISTING

<160> NUMBER OF SEQ ID NOS: 8

<210> SEQ ID NO 1
<211> LENGTH: 21
<212> TYPE: DNA
<213> ORGANISM: Artificial Sequence
<220> FEATURE:
<223> OTHER INFORMATION: Synthetically generated primer

<400> SEQUENCE: 1
ggcaacgcaa catgataaga c                     21

<210> SEQ ID NO 2
<211> LENGTH: 20
<212> TYPE: DNA
<213> ORGANISM: Artificial Sequence
<220> FEATURE:
<223> OTHER INFORMATION: Synthetically generated primer

<400> SEQUENCE: 2
gttcaagggt tgcacagctt                       20

<210> SEQ ID NO 3
<211> LENGTH: 19
<212> TYPE: DNA
<213> ORGANISM: Artificial Sequence
<220> FEATURE:

-continued

```
<223> OTHER INFORMATION: Synthetically generated primer

<400> SEQUENCE: 3
atcgtgaaca accaagtga                                              19

<210> SEQ ID NO 4
<211> LENGTH: 20
<212> TYPE: DNA
<213> ORGANISM: Artificial Sequence
<220> FEATURE:
<223> OTHER INFORMATION: Synthetically generated primer

<400> SEQUENCE: 4
gttcaagggt tgcacagctt                                             20

<210> SEQ ID NO 5
<211> LENGTH: 20
<212> TYPE: DNA
<213> ORGANISM: Artificial Sequence
<220> FEATURE:
<223> OTHER INFORMATION: Synthetically generated primer

<400> SEQUENCE: 5
aacagtatcc taccagccca                                             20

<210> SEQ ID NO 6
<211> LENGTH: 20
<212> TYPE: DNA
<213> ORGANISM: Artificial Sequence
<220> FEATURE:
<223> OTHER INFORMATION: Synthetically generated primer

<400> SEQUENCE: 6
cctctacttc ttcttcgggt                                             20

<210> SEQ ID NO 7
<211> LENGTH: 18
<212> TYPE: DNA
<213> ORGANISM: Artificial Sequence
<220> FEATURE:
<223> OTHER INFORMATION: Synthetically generated primer

<400> SEQUENCE: 7
gacggaccct ctggaaaa                                               18

<210> SEQ ID NO 8
<211> LENGTH: 19
<212> TYPE: DNA
<213> ORGANISM: Artificial Sequence
<220> FEATURE:
<223> OTHER INFORMATION: Synthetically generated primer

<400> SEQUENCE: 8
accagctgat gagcttgac                                              19
```